United States Patent
AlSinan et al.

(10) Patent No.: US 11,788,978 B2
(45) Date of Patent: Oct. 17, 2023

(54) METHOD AND SYSTEM FOR DETERMINING GEOLOGICAL MODELS USING SPATIAL PROPERTIES BASED ON NUCLEAR MAGNETIC RESONANCE DATA

(71) Applicant: SAUDI ARABIAN OIL COMPANY, Dhahran (SA)

(72) Inventors: Marwah Mufid AlSinan, Al Qatif (SA); Hyung Tae Kwak, Dhahran (SA); Jun Gao, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/454,720

(22) Filed: Nov. 12, 2021

(65) Prior Publication Data

US 2023/0152253 A1    May 18, 2023

(51) Int. Cl.
   *G01N 24/08*      (2006.01)
   *G01R 33/46*      (2006.01)
   (Continued)

(52) U.S. Cl.
   CPC ......... *G01N 24/081* (2013.01); *E21B 49/003* (2013.01); *G01N 33/24* (2013.01); *G01R 33/46* (2013.01); *E21B 2200/20* (2020.05)

(58) Field of Classification Search
   CPC .... G01N 24/081; G01N 33/24; E21B 49/003; E21B 2200/20; G01R 33/46
   See application file for complete search history.

(56) References Cited

U.S. PATENT DOCUMENTS

| 4,719,423 A | 1/1988 | Vinegar et al. |
| 5,237,854 A | 8/1993 | Jones |
| (Continued) | | |

FOREIGN PATENT DOCUMENTS

WO    2020185801 A1    9/2020

OTHER PUBLICATIONS

Skalinski, M. and Kenter, J., "Carbonate petrophysical rock typing: integrating geological attributes and petrophysical properties while linking with dynamic behaviour", Geological Society; Jan. 1, 2015 (31 pages).

(Continued)

*Primary Examiner* — Jay Patidar
(74) *Attorney, Agent, or Firm* — Osha Bergman Watanabe & Burton LLP

(57) ABSTRACT

A method may include obtaining first nuclear magnetic resonance (NMR) data for a saturated core sample regarding a geological region of interest. The method may further include determining, using the first NMR data, spatial porosity data based on the saturated core sample. The spatial porosity data may describe various porosity values as a function of a sampling position of the saturated core sample. The method may further include obtaining second NMR data for a desaturated core sample regarding the geological region of interest. The method may further include determining, using the second NMR data, spatial permeability data based on the desaturated core sample. The method may further include determining a geological model for the geological region of interest using the spatial porosity data, the spatial permeability data, and a fitting process.

20 Claims, 9 Drawing Sheets

(51) Int. Cl.
*E21B 49/00* (2006.01)
*G01N 33/24* (2006.01)

(56) References Cited

U.S. PATENT DOCUMENTS

| | | | |
|---|---|---|---|
| 6,229,308 | B1 | 5/2001 | Freedman |
| 6,646,437 | B1 | 11/2003 | Chitale et al. |
| 6,859,034 | B2 | 2/2005 | Chen |
| 9,081,117 | B2 | 7/2015 | Wu et al. |
| 9,551,769 | B2 | 1/2017 | Fordham et al. |
| 9,702,953 | B1 | 7/2017 | Xiao et al. |
| 10,436,865 | B2 | 10/2019 | Washburn |
| 10,900,915 | B2 | 1/2021 | Gawankar et al. |
| 2008/0221800 | A1 | 9/2008 | Gladkikh et al. |
| 2009/0043510 | A1 | 2/2009 | Allen et al. |
| 2009/0177403 | A1 | 7/2009 | Gzara |
| 2011/0153216 | A1 | 6/2011 | Coope et al. |
| 2011/0198078 | A1 | 8/2011 | Harrigan et al. |
| 2014/0055134 | A1 | 2/2014 | Fordham et al. |
| 2014/0285196 | A1 | 9/2014 | Liu et al. |
| 2018/0259466 | A1 | 9/2018 | Mitchell et al. |
| 2019/0033239 | A1 | 1/2019 | Gao et al. |
| 2019/0317034 | A1 | 10/2019 | Kwak et al. |
| 2020/0158907 | A1 | 5/2020 | Li et al. |
| 2020/0166449 | A1 | 5/2020 | Green et al. |
| 2020/0408090 | A1 | 12/2020 | Kadayam Viswanathan et al. |
| 2021/0072171 | A1* | 3/2021 | Kuang ............... G01R 33/448 |

OTHER PUBLICATIONS

Coates et al.; "The MRIL In Conoco 33-1 An Investigation of a New Magnetic Resonance Imaging Log", SPWLA-1991-DD; Society of Petrophysicists and Well Log Analysts; Jun. 16, 1991; pp. 1-24 (24 pages).

Kenywon, W. E.; "Petrophysical Principles of Applications of NMR Logging", The Log Analyst; vol. 38; Issue 2; Mar. 1, 1997; pp. 21-43 (23 pages).

Petrov et al.; "T2 distribution mapping profiles with phase-encode MRI", Journal of Magnetic Resonance; vol. 209; Dec. 19, 2010; pp. 39-46 (8 pages).

Coates et al.; "A New Characterization of Bulk-Volume Irreducible Using Magnetic Resonance", SPWLA-1997-QQ; Society of Petrophysicists and Well Log Analysts; Jun. 1997; pp. 51-63 (13 pages).

Hassler et al.; "Measurement of Capillary Pressure in Small Core Samples", SPE-945114-G; Society of Petroleum Engineers; vol. 160; Dec. 1945; pp. 114-123 (10 pages).

Brooks, R. H. and Corey, A. T.; "Hydraulic Properties of Porous Media", Hydrology Papers, Colorado State University; Mar. 1964; pp. 1-37 (37 pages).

"Least Squares Fittings;" Oct. 13, 2021; pp. 1-4; Retrieved from the Internet: URL: https://mathworld.wolfram.com/LeastSquaresFitting.html (4 pages).

Jones, S. C.; "A New, Fast, Accurate Pressure-Decay Probe Permeameter", SPE-24757-PA; Society of Petroleum Engineers; vol. 9, Issue 3; Sep. 1, 1994; pp. 193-199 (7 pages).

Timur, A.; "An Investigation of Permeability, Porosity, & Residual Water Saturation Relationships For Sandstone Reservoirs", SPWLA-1968-VLXN4A2; The Log Analyst; vol. 9; Issue 4; Jul. 1968; pp. 8-17 (10 pages).

Lis-Sledziona, A.; "Petrophysical rock typing and permeability prediction in tight sandstone reservoir", Acta Geophysica; vol. 67; Aug. 29, 2019; pp. 1895-1911 (17 pages).

Timur, A.; "Pulsed Nuclear Magnetic Resonance Studies of Porosity, Movable Fluid, and Permeability of Sandstones"; Journal of Petroleum Technology; vol. 21; Issue 6; Jun. 1, 1969; pp. 775-786 (12 pages).

Freedman et al.; "Wettability, Saturation, and Viscosity From NMR Measurements", SPE-87340-PA; SPE Journal; vol. 8; Issue 4; Dec. 1, 2003; pp. 317-327 (11 pages).

Oraby, M. E. and Eubanks, D. L.; "Determination Of Irreducible Water Saturation Using Magnetic Resonance Imaging Logs (MRIL): A Case Study From East Texas, USA", SPE-37772; Society of Petroleum Engineers; Mar. 1997; pp. 155-162 (8 pages).

Gonzalez, A.; "Reliable Measurement of Saturation-dependent Relative Permeability in Tight Gas Sand Formations", Petrophysics; vol. 61; No. 3; Jun. 2020; pp. 286-302 (17 pages).

Vashaee et al.; "A comparison of magnetic resonance methods for spatially resolved T2 distribution measurements in porous media", Measurement Science and Technology; vol. 26; Apr. 9, 2015; pp. 1-16 (16 pages).

* cited by examiner

METHOD AND SYSTEM FOR DETERMINING GEOLOGICAL MODELS USING SPATIAL PROPERTIES BASED ON NUCLEAR MAGNETIC RESONANCE DATA

BACKGROUND

A subsurface formation may be analyzed using various measurements obtained from well logs and core samples. For example, these measurements may be used to calculate porosity, permeability, and other properties of a reservoir formation. However, in many situations, an accurate depiction of the subsurface formation may require multiple wells and many measurements to have sufficient data for characterizing the formation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method that includes obtaining, by a computer processor, first nuclear magnetic resonance (NMR) data for a saturated core sample regarding a geological region of interest. The method further includes determining, by the computer processor and using the first NMR data, spatial porosity data based on the saturated core sample. The spatial porosity data describe various porosity values as a function of a sampling position of the saturated core sample. The method further includes obtaining, by the computer processor, second NMR data for a desaturated core sample regarding the geological region of interest. The method further includes determining, by the computer processor and using the second NMR data, spatial permeability data based on the desaturated core sample. The spatial permeability data describe various permeability values as a function of the sampling position of the desaturated core sample. The method further includes determining, by the computer processor, a geological model for the geological region of interest using the spatial porosity data, the spatial permeability data, and a fitting process.

In general, in one aspect, embodiments relate to a system that includes a nuclear magnetic resonance (NMR) spectroscopy tool and a reservoir simulator that includes a computer processor. The reservoir simulator is coupled to the NMR spectroscopy tool. The reservoir simulator obtains, using the NMR spectroscopy tool, first nuclear magnetic resonance (NMR) data for a saturated core sample regarding a geological region of interest. The reservoir simulator determines, using the first NMR data, spatial porosity data based on the saturated core sample. The spatial porosity data describe various porosity values as a function of a sampling position of the saturated core sample. The reservoir simulator obtains, using the NMR spectroscopy tool, second NMR data for a desaturated core sample regarding the geological region of interest. The reservoir simulator determines, using the second NMR data, spatial permeability data based on the desaturated core sample. The spatial permeability data describe various permeability values as a function of the sampling position of the desaturated core sample. The reservoir simulator determines a geological model for the geological region of interest using the spatial porosity data, the spatial permeability data, and a fitting process.

In general, in one aspect, embodiments relate to a non-transitory computer readable medium storing instructions executable by a computer processor. The instructions obtain first nuclear magnetic resonance (NMR) data for a saturated core sample regarding a geological region of interest. The instructions determine, using the first NMR data, spatial porosity data based on the saturated core sample. The spatial porosity data describe various porosity values as a function of a sampling position of the saturated core sample. The instructions obtain second NMR data for a desaturated core sample regarding the geological region of interest. The instructions determine, using the second NMR data, spatial permeability data based on the desaturated core sample. The spatial permeability data describe various permeability values as a function of the sampling position of the desaturated core sample. The instructions determine a geological model for the geological region of interest using the spatial porosity data, the spatial permeability data, and a fitting process.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
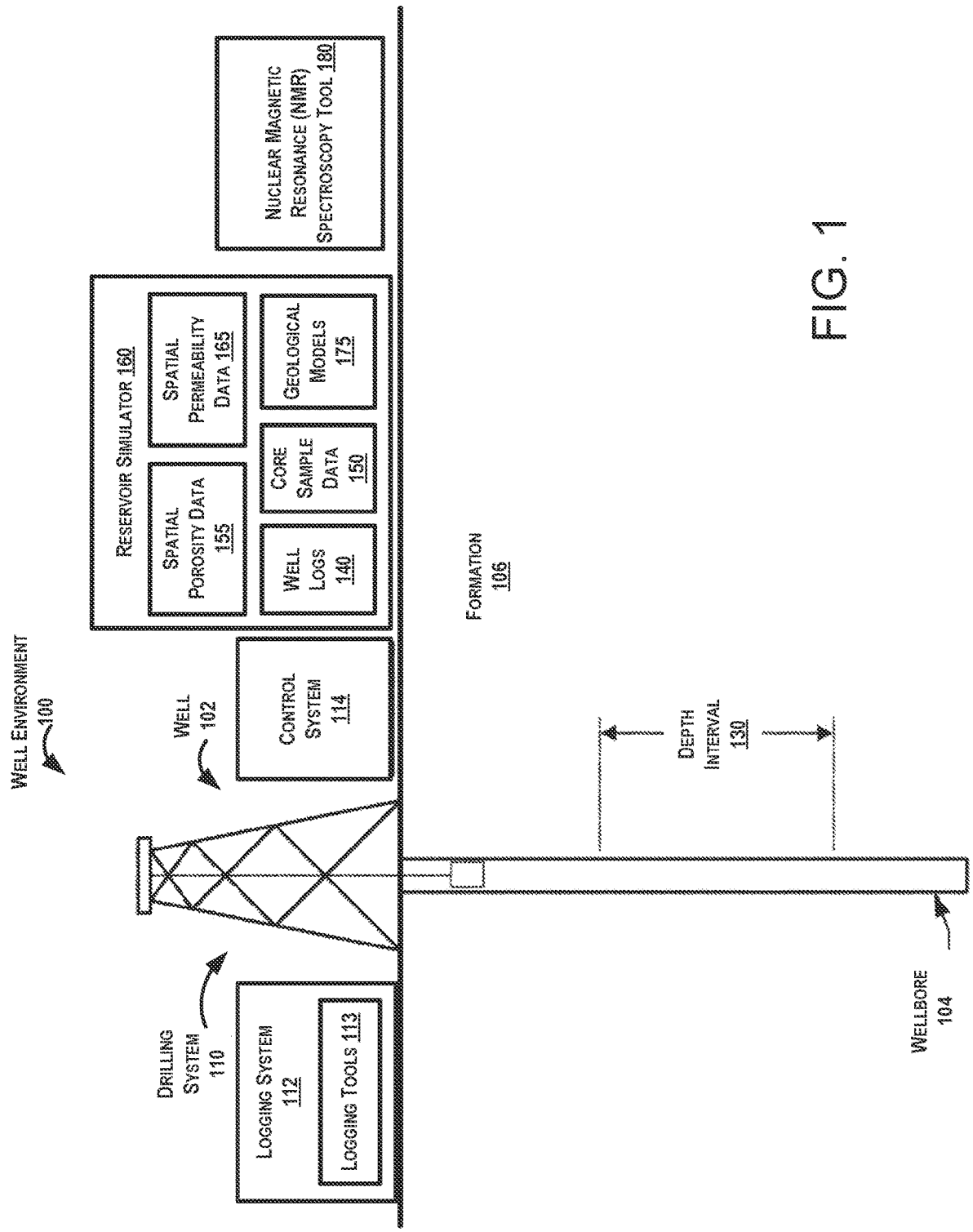
FIG. 1 show a system in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the disclosure include systems and methods for determine rock type information and other geological model data using spatial porosity and spatial permeability values based on nuclear magnetic resonance (NMR) data. Rock type information may include a specific pore type for a given core sample (also called a "core plug") that is obtained from a well. In some embodiments, for example, spatial and directional T2 NMR measurements are obtained for a saturated core sample and the same core sample following a desaturation operation (e.g., using a centrifuge or porous plate). This NMR data may be used to generate porosity-permeability cross-plots or determine other relationships between spatial porosity data and spatial permeability data. Based on these porosity-permeability cross-plots, for example, a particular rock type may be identified for the core sample. Rather than using averaged NMR measurements for an entire core sample, various petrophysical properties may be linked to different geological attributes and diagenetic modifications using NMR data at different sampling locations and/or sampling directions of a core sample.

By obtaining more data points per core sample, the petrophysical properties obtained from the NMR data may be more representative of a particular reservoir. This rock type data may have various practical applications, such as use in predicting reservoir properties in uncored wells. In heterogeneous formations, this rock type data may also provide better modeling techniques for complex pore structures, such as formations based on carbonate, fluvial and glacial sandstones. By obtaining multiple measurements in different sampling directions on the same core sample, petrophysical rock types may be determined for anisotropic formations, such as formations with thin cross-bedding. Likewise, a reservoir simulator may have an additional advantage of being able to determine a particular rock type for a geological region from a single core sample rather than a group of core samples.

FIG. 1 shows a schematic diagram in accordance with one or more embodiments. As shown, FIG. 1 illustrates a well environment (100) that may include a well (102) having a wellbore (104) extending into a formation (106). The wellbore (104) may include a bored hole that extends from the surface into a target zone of the formation (106), such as a reservoir. The formation (106) may include various formation characteristics of interest, such as formation porosity, formation permeability, resistivity, density, water saturation, and the like. Porosity may indicate how much space exists in a particular rock within an area of interest in the formation (106), where oil, gas, and/or water may be trapped. Permeability may indicate the ability of liquids and gases to flow through the rock within the area of interest. Resistivity may indicate how strongly rock and/or fluid within the formation (106) opposes the flow of electrical current. For example, resistivity may be indicative of the porosity of the formation (106) and the presence of hydrocarbons. More specifically, resistivity may be relatively low for a formation that has high porosity and a large amount of water, and resistivity may be relatively high for a formation that has low porosity or includes a large amount of hydrocarbons. Water saturation may indicate the fraction of water in a given pore space.

Keeping with FIG. 1, the well environment (100) may include reservoir simulator (160) and various well systems, such as a drilling system (110), a logging system (112), and a control system (114). The drilling system (110) may include a drill string, drill bit, a mud circulation system and/or the like for use in boring the wellbore (104) into the formation (106). Well systems may also include production systems that include production trees, production valves, downhole sensors, wellhead sensors, etc. The control system (114) may include hardware and/or software for managing drilling operations or production operations. For example, the control system (114) may include one or more programmable logic controllers (PLCs) that include hardware and/or software with functionality to control one or more processes performed by the drilling system (110). Specifically, a programmable logic controller may control valve states, fluid levels, pipe pressures, warning alarms, and/or pressure releases throughout a drilling rig. In particular, a programmable logic controller may be a ruggedized computer system with functionality to withstand vibrations, extreme temperatures, wet conditions, and/or dusty conditions, for example, around a drilling rig. A logging system may be similar to a control system with a specific focus on managing one or more logging tools.

Turning to the reservoir simulator (160), a reservoir simulator (160) may include hardware and/or software with functionality for storing and analyzing well logs (140), core sample data (150), spatial porosity data (155), spatial permeability data (165), seismic data, and/or other types of data to generate and/or update one or more geological models (175). Geological models may include geochemical or geomechanical models that describe structural relationships within a particular geological region. Likewise, a geological model may identify one or more rock types associated with one or more geological regions (e.g., formation (106)). Examples of rock types may include one or more depositional rock types (e.g., where a geological region is based on a depositional environment), rock types that include similar diagenetic processes, rock types based on similar geological trends, and/or rock types based on similar reservoir properties. For example, a rock type may correspond to an irreducible water saturation, a residual oil saturations, rock permeability, capillary pressure, maximum capillary pressure heights, relative permeabilities, and rock classes. Likewise, rock types may be based on static reservoir properties as well as dynamic reservoir properties.

While the reservoir simulator (160) is shown at a well site, in some embodiments, the reservoir simulator (160) or other components in FIG. 1 may be remote from a well site. In some embodiments, the reservoir simulator (160) is implemented as part of a software platform for the control system (114). The software platform may obtain data acquired by the drilling system (110) and logging system (112) as inputs, which may include multiple data types from multiple sources. The software platform may aggregate the data from these systems (110, 112) in real time for rapid analysis. In some embodiments, the control system (114), the logging system (112), the reservoir simulator (160), and/or a user device coupled to one of these systems may include a computer system that is similar to the computer system (1002) described below with regard to FIG. 10 and the accompanying description.

In some embodiments, petrophysical rock typing is used for distributing reservoir properties, such as porosity, permeability and water saturation, in the geological model. These reservoir properties may impact the predicted hydrocarbon reserves and recovery in production operations. In particular, rock typing may be used to describe geologically complicated formations, such as carbonate formations, fluvial formations, and glacial sandstone formations with highly heterogeneous pore structures. Several processes may be used for defining rock types, such as depositional-based rock-typing, pore type-based rock typing, dynamic rock typing, porosity and permeability partitioning processes using core samples and well logs, and integrated rock typing approaches. Turning to porosity and permeability partitioning processes, some embodiments use well logs and average measurements from core samples to determine petrophysical properties in cored wells. For example, porosity and permeability partitioning may be used to describe sandstone and carbonate reservoirs with predominant depositional control and few diagenetic modifications.

The logging system (112) may include one or more logging tools (113) for use in generating well logs of the formation (106). For example, a logging tool may be lowered into the wellbore (104) to acquire measurements as the tool traverses a depth interval (130) (e.g., a targeted reservoir section) of the wellbore (104). The plot of the logging measurements versus depth may be referred to as a "log" or "well log". Well logs (140) may provide depth measurements of the well (104) that describe such reservoir characteristics as formation porosity, formation permeability, resistivity, water saturation, and the like. The resulting logging measurements may be stored and/or processed, for example, by the control system (114), to generate corresponding well logs for the well (102). A well log (140) may include, for example, a plot of a logging response time versus true vertical depth (TVD) across the depth interval (130) of the wellbore (104).

Turning to examples of logging techniques, multiple types of logging techniques are available for determining various reservoir characteristics (e.g., wireline logging, logging-while-drilling (LWD), and measurement-while-drilling (MWD)). For example, a nuclear magnetic resonance (NMR) analysis tool (e.g., an NMR logging tool or an NMR spectroscopy tool (180)) may measure the induced magnetic moment of hydrogen nuclei (i.e., protons) contained within the fluid-filled pore space of porous media (e.g., reservoir rocks). Thus, NMR data (e.g., NMR logs or NMR laboratory results) may measure the magnetic response of fluids present in the pore spaces of the reservoir rocks. In so doing, NMR data may measure both porosity and permeability, as well as the types of fluids present in the pore spaces. Thus, NMR logging may be a subcategory of electromagnetic logging that responds to the presence of hydrogen protons rather than a rock matrix. Because hydrogen protons may occur primarily in pore fluids, NMR data may directly or indirectly measure the volume, composition, viscosity, and distribution of pore fluids.

NMR analysis techniques may determine multiple signals for analyzing a geological region or core sample. First, an NMR analysis may determine spin-lattice relaxation values or a T1 signal amplitude that is measured from the buildup of magnetization along a static applied magnetic field. For example, a T1 value may be the time needed to reach 63% of the maximum magnetization possible at its final value. Three times of a T1 value may be equal to 95% of polarization. Large values of T1 may indicate weak coupling between fluid and a slow approach to the magnetic equilibrium. However, small T1 values may show strong coupling to quickly reach the equilibrium state. Thus, T1 signal values may be mainly related to pore size and viscosity. Likewise, a T1 signal may be measured using inversion recovery or saturation recovery, where the T1 signal may be characterized as the loss of resonance intensity following a pulse excitation. Inversion recovery may include a 180° spin inversion followed by a variable recovery time and then a 90° read pulse. On the other hand, saturation recovery may use a 90° pulse, followed by a 90° read pulse.

Furthermore, an NMR analysis may also determine transverse relaxation values or a T2 signal amplitude that describes the decay of an excited magnetization perpendicular to an applied magnetic field. More specifically, a T2 signal may be determined using a spin-echo technique, where hydrogen protons are first tipped into the transverse plane by a 90° RF pulse and then inverted by a subsequent 180° pulse at a fixed-time interval to rephase the dephasing protons. The T2 signal may refer to the decaying time for hydrogen protons to complete dephasing. Likewise, NMR measurements may be illustrated as a T2 signal amplitude versus time and determine a distribution of porosity components (i.e., a T2 distribution) as a function of their T2 times. Thus, a T2 signal amplitude may be proportional to hydrogen content within a core sample and thus may determine porosity independent of the rock matrix. Both relaxation times may provide information for determining pore-size information and pore-fluid properties, especially viscosity.

Keeping with T2 signals, NMR measurements may use a T2 cutoff value (which may be referred to as a "$T_{2c}$ value" or a "$T_{2cutoff}$ value") in order to divide effective porosity into movable and irreducible fluid saturations. A T2 cutoff value may be the maximum T2 signal amplitude for a portion of porosity that is occupied by immovable fluids. Accordingly, the T2 cutoff value may distinguish free fluid volume (FFV) from non-movable fluid or bound fluid volume (BFV) in a geological region or core sample. In a T2 distribution, a BVI value may include T2 amplitudes in the spectrum having T2 values less than the T2 cutoff value. In other words, a T2 cutoff value may be the sum of porosities whose T2 amplitude is less than the T2 cutoff value and consequently an FFI value may be the sum of T2 amplitudes that are greater than the T2 cutoff value. Likewise, T2 signal values above the T2 cutoff value may indicate large pores that are potentially capable of production. On the other hand, T2 signal values below the T2 cutoff value may indicate small pores containing fluid trapped by capillary pressure with little production capacity. Therefore, the T2 cutoff value may be used to analyze the ratio of irreducible fluid and movable fluid in porous rock. Accordingly, a T2 value distribution may also provide a permeability prediction of a geological region.

Various reservoir parameters may be determined by analyzing NMR data, such as T2 signal data. For example, NMR porosity ("MPHI") may be determined by an integral of a saturated T2 distribution curve, which may be the area under a T2 signal curve. Likewise, a core sample may be centrifuged in order to repeat an NMR measurement to determine a value of the bulk volume irreducible of water (BVI) or amount of irreducible fluid in the core sample. A free fluid index (FFI) value may be the difference between total porosity and the BVI value. BVI values may correspond to the immovable or bound water in a formation, such as a capillary bound water. Thus, BVI may be a function of the pore-throat size distribution, where high threshold pressure due to smaller pore throats retains the fluids in the pores. BVI values may be determined using a cutoff-BVI (CBVI) model or a spectral BVI (SBVI) model, for example.

In some embodiments, the T2 cutoff value may be a constant value applied throughout a particular formation. For example, a T2 cutoff value of 33 ms and another T2 cutoff value of 22.6 ms have been used for analyzing sandstone formations. In another example, a T2 cutoff value of 33 ms has been used with a clastic reservoir to estimate BFV values and FFV values. In another example, four T2 cutoff values of 10 ms, 15 ms, 20 ms, and 33 ms may be used to determine four sets of bound fluid volume (BFV) and free fluid volume (FFV) values. However, T2 cutoff values may vary in different formations and in different fields due to reservoir temperatures, surface relaxivity of a rock surface, and other field factors. In particular, surface relaxivity may depend on mineralogy of a particular formation, such as the presence of paramagnetic/ferromagnetic minerals and adsorbed water in the formation.

Turning to laboratory NMR analyses, one or more laboratory NMR analyses may be performed using one or more NMR spectroscopy tools (e.g., NMR spectroscopy tool (180)). For example, an NMR spectroscopy tool may include various types of NMR spectrometers, where a NMR spectrometer may include a magnet module with one or more permanent magnets, a scan control system that includes various scan coils, and an oscilloscope for performing adjustments for signal amplitudes and phases. NMR spectroscopy tools may also include various multi-frequency antennas and probes. Likewise, NMR spectroscopy tools may also include automated laboratory apparatuses that perform sample preparation, automatic probe tuning, and data acquisition and NMR data processing. Using a laboratory, an NMR analysis may enable control of a testing environment (e.g., for managing saturating and desaturation operations of fluid within a core sample). Also, laboratory NMR measurements may be conducted at higher magnetic field than logging NMR techniques. Laboratory NMR analyses may also be non-destructive and provide spatial petrophysical properties (e.g., porosity and permeability) of a core sample.

Returning to logging tools, other types of logging techniques may also be used to analyze a geological region. For determining permeability, another type of logging may be used that is called spontaneous potential (SP) logging. SP logging may determine the permeabilities of rocks in the formation (106) by measuring the amount of electrical current generated between drilling fluid produced by the drilling system (110) and formation water that is held in pore spaces of the reservoir rock. Porous sandstones with high permeabilities may generate more electricity than impermeable shales. Thus, SP logs may be used to identify sandstones from shales. To determine porosity in the formation (106), the logging system (112) may measure the speed that acoustic waves travel through rocks in the formation (106). This type of logging may generate borehole compensated (BHC) logs, which are also called sonic logs. In general, sound waves may travel faster through high-density shales than through lower-density sandstones. Likewise, density logging may also determine porosity measurements by directly measuring the density of the rocks in the formation (106). Furthermore, neutron logging may determine porosity measurements by assuming that the reservoir pore spaces within the formation (106) are filled with either water or oil and then measuring the amount of hydrogen atoms (i.e., neutrons) in the pores. Other types of logging are also contemplated, such as resistivity logging and dielectric logging.

Reservoir characteristics may be determined using coring (e.g., physical extraction of rock specimens) to produce core samples for core analyses. Coring operations may include physically extracting a rock specimen from a region of interest within the wellbore (104) for detailed laboratory analysis. For example, when drilling an oil or gas well, a coring bit may cut core samples (or "cores" or "core specimens" or "core plugs") from the formation (106) and bring the core samples to the surface, and these core specimens may be analyzed at the surface (e.g., in a laboratory) to determine various characteristics of the formation (106) at the location where the specimen was obtained.

Turning to various coring technique examples, conventional coring may include collecting a cylindrical specimen of rock from the wellbore (104) using a core bit, a core barrel, and a core catcher. The core bit may have a hole in its center that allows the core bit to drill around a central cylinder of rock. Subsequently, the resulting core specimen may be acquired by the core bit and disposed inside the core barrel. More specifically, the core barrel may include a special storage chamber within a coring tool for holding the core specimen. Furthermore, the core catcher may provide a grip to the bottom of a core and, as tension is applied to the drill string, the rock under the core breaks away from the undrilled formation below coring tool. Thus, the core catcher may retain the core specimen to avoid the core specimen falling through the bottom of the drill string.

Turning to geosteering, geosteering may be used to position the drill bit or drill string of the drilling system (110) relative to a boundary between different subsurface layers (e.g., overlying, underlying, and lateral layers of a pay zone) during drilling operations. In particular, measuring rock properties during drilling may provide the drilling system (110) with the ability to steer the drill bit in the direction of desired hydrocarbon concentrations. As such, a geosteering system may use various sensors located inside or adjacent to the drill string to determine different rock formations within a well path. In some geosteering systems, drilling tools may use resistivity or acoustic measurements to guide the drill bit during horizontal or lateral drilling. Likewise, a well path of a wellbore (104) may be updated by the control system (114) using a geological model (e.g., one of the geological models (175)). For example, a control system (114) may communicate geosteering commands to the drilling system (110) based on well data updates that are further adjusted by the reservoir simulator (160) using a geological model. As such, the control system (114) may generate one or more control signals for drilling equipment (or a logging system may generate for logging equipment) based on an updated well path design and/or a geological model.

While FIG. 1 show various configurations of components, other configurations may be used without departing from the scope of the disclosure. For example, various components in FIG. 1 may be combined to create a single component. As another example, the functionality performed by a single component may be performed by two or more components.

Figure 2:
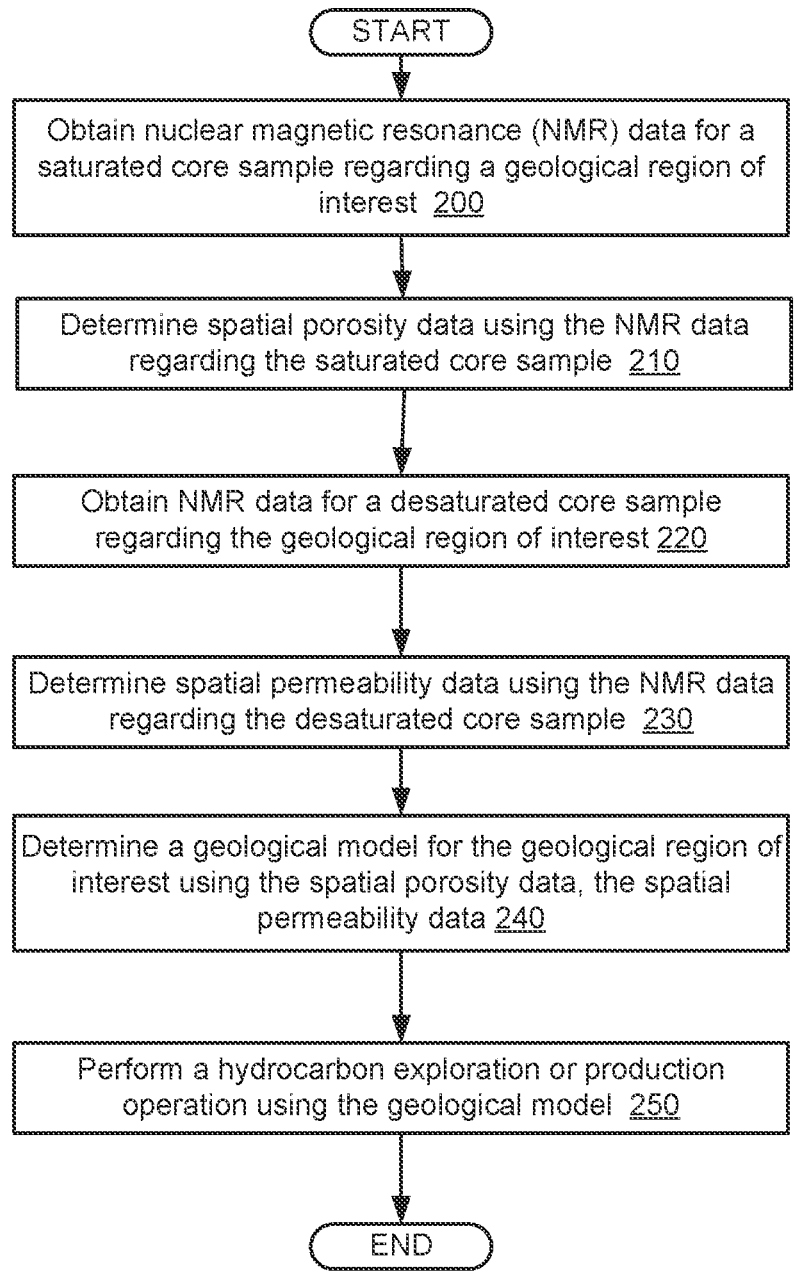
FIG. 2 shows a flowchart in accordance with one or more embodiments.

Turning to FIG. 2, FIG. 2 shows a flowchart in accordance with one or more embodiments. Specifically, FIG. 2 describes a general method for generating and/or using a geological model based on spatial NMR data. One or more blocks in FIG. 2 may be performed by one or more components (e.g., reservoir simulator (160) or NMR spectroscopy tool (180)) as described in FIG. 1. While the various blocks in FIG. 2 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 200, NMR data are obtained for a saturated core sample regarding a geological region of interest in accordance with one or more embodiments. For example, NMR data may describe a distribution of T2 relaxation times at different sampling locations of a saturated core sample. Likewise, NMR data may be acquired using an NMR spectroscopy tool during a laboratory analysis similar to the NMR spectroscopy tools described above in FIG. 1 and the accompanying description. A geological region of interest may be a portion of a geological area or volume that includes one or more formations of interest desired or selected for analysis, e.g., for determining location of hydrocarbons or for reservoir development purposes. In particular, the geological region of interest may include multiple wells already drilled as well as locations of one or more potential wells for drilling.

Furthermore, a saturation operation may be performed on a core sample that includes soaking the core sample in a predetermined fluid. In particular, porous media of the core sample may be fully or partially saturated in a saturation solution, e.g., $H_2O$ or a 3% KCL (i.e., potassium chloride) brine solution if the porous media is sandstone to prevent clay from swelling. The saturation operation may soak the core sample by submersing the porous media in a tub of the saturation solution for several hours to allow the fluid to permeate the voids within the porous media. A soaking-type saturation operation may be used for porous media that have a relatively high permeability or porosity values. In some embodiments, a saturation operation includes injecting the saturation solution into the porous media. For example, an injection saturation operation may include placing the porous media into a pressure cell and operating the pressure cell to elevate the pressure of the saturation solution around the porous media to force the fluid to permeate the voids within the core sample. An injection-type saturation operation may work well for porous media that have a relatively low permeability or porosity value (sometime referred to as "tight porous media").

In Block 210, spatial porosity data are determined using NMR data regarding a saturated core sample in accordance with one or more embodiments. For example, a reservoir simulator may acquire spatial T2 distribution data of a fully $H_2O$ saturated core sample for one or more predetermined orientations. Spatial T2 distribution data may be acquired by T2 mapping an NMR pulse sequence, such as spin echo single point imaging.

In some embodiments, spatial porosity data is a function of sampling position of a core sample. For example, NMR data may be acquired according to one or more sampling directions (e.g., a horizontal axis or a vertical axis that is centered on a core sample) and various sampling locations for the core sample. In particular, a saturated core sample or a desaturated core sample may be divided into various core slices, where each core slice may be analyzed by an NMR spectroscopy tool. A core slice may correspond to a particular volume section and the number of core slices may be based on a desired precision of spatial porosity data or spatial permeability data.

Figure 3A:
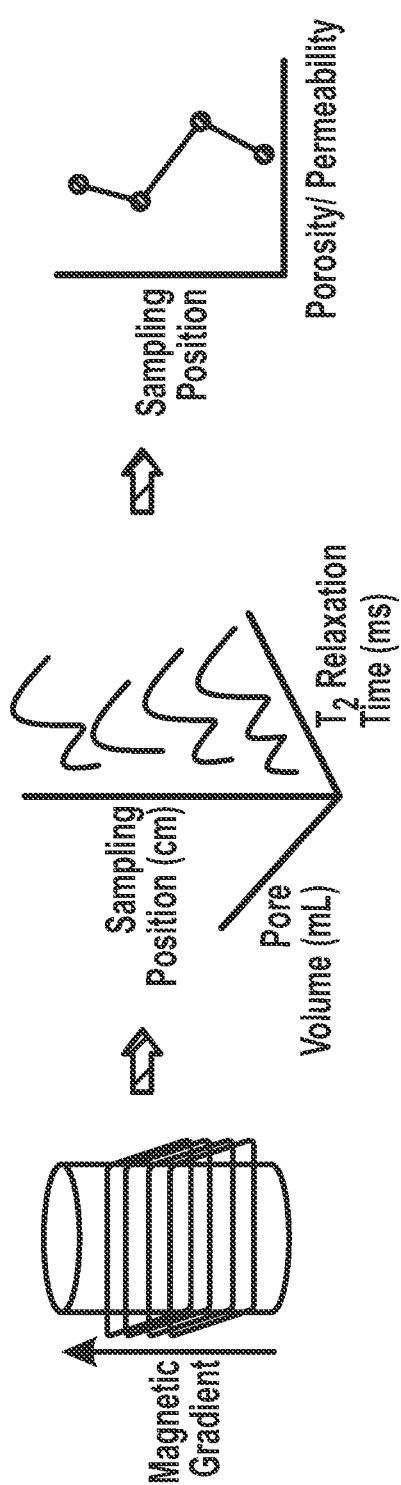
FIGS. 3A, 3B, 4, 5, 6, 7, 8, and 9 show examples in accordance with one or more embodiments.
Figure 3B:
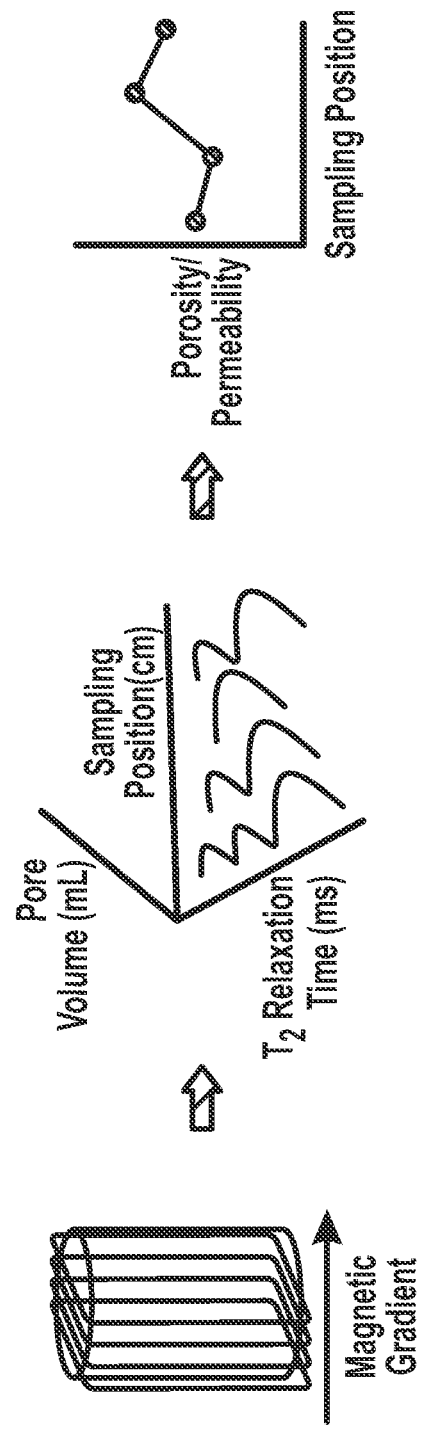

Turning to FIGS. 3A and 3B, FIGS. 3A and 3B shows spatial porosity data and spatial permeability data in accordance with one or more embodiments. In FIG. 3A, the schematic illustration of porosity and brine permeability profiles are shown in different direction, where the square planes on the core sample describe sampling areas for spatial porosity data and spatial permeability data. As such, multiple magnetic gradients are detected at different sampling positions along a horizontal axis using NMR data. Based on a sampling position, spatial porosity data or spatial permeability data may be described in a profile as a function of sampling position. In FIG. 3B, a similar procedure is performed where multiple magnetic gradients are detected at different sampling positions along a vertical axis.

Figure 4:
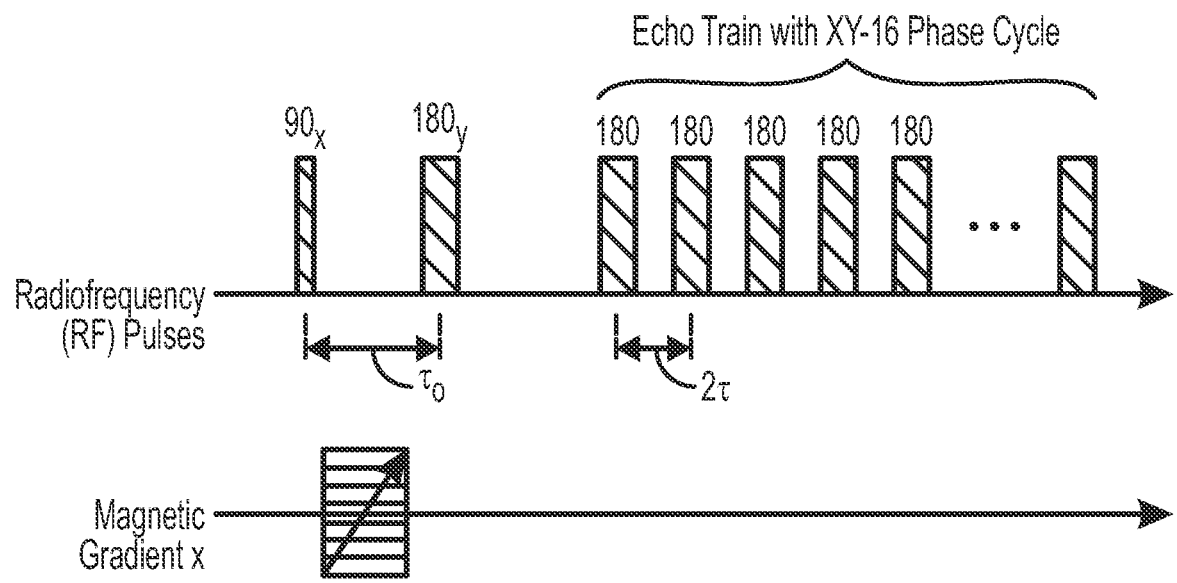

Turning to FIG. 4, FIG. 4 shows a pulse diagram of an NMR pulse sequence in accordance with some embodiments. In FIG. 4, various radio frequency electrical pulses are encoded according to an echo train phase cycle, where $\tau_o$ refers to a phase encoding time. For example, an echo train acquisition (ETA) may be used in magnetic resonance spectroscopy where a pulse sequence is repeated with ever-increasing delay times. The pulse sequence may continue for as long as an allotted repeat time. For example, a spin echo may be produced halfway between 180° pulses. The core sample may be pulsed again iteratively at a sampling position with 180° to cause another spin echo during the echo train acquisition. Thus, a train of spin echoes may be produced by refocusing a predetermined magnetization at a portion of a core sample. With each magnetization iteration, a spin echo amplitude may decay away due to spin-spin relaxation. Thus, a magnetic gradient may be determined for NMR data accordingly.

Keeping with Block 210, in some embodiments, a porosity profile of a core sample is determined from the spatial porosity data. For example, a porosity profile may be determined using the following equation:

Porosity ($\phi$), $\qquad$ Equation (1)

$$\% = \frac{\text{Pore Volume at the Sampling Position (mL)}}{\text{Volume of the sampled slice (mL)}} \times 100$$

where the porosity profile may include a curve based on a ratio between a pore volume at a particular sampling position of a core sample with respect to a total volume of the core sample.

Figure 5:
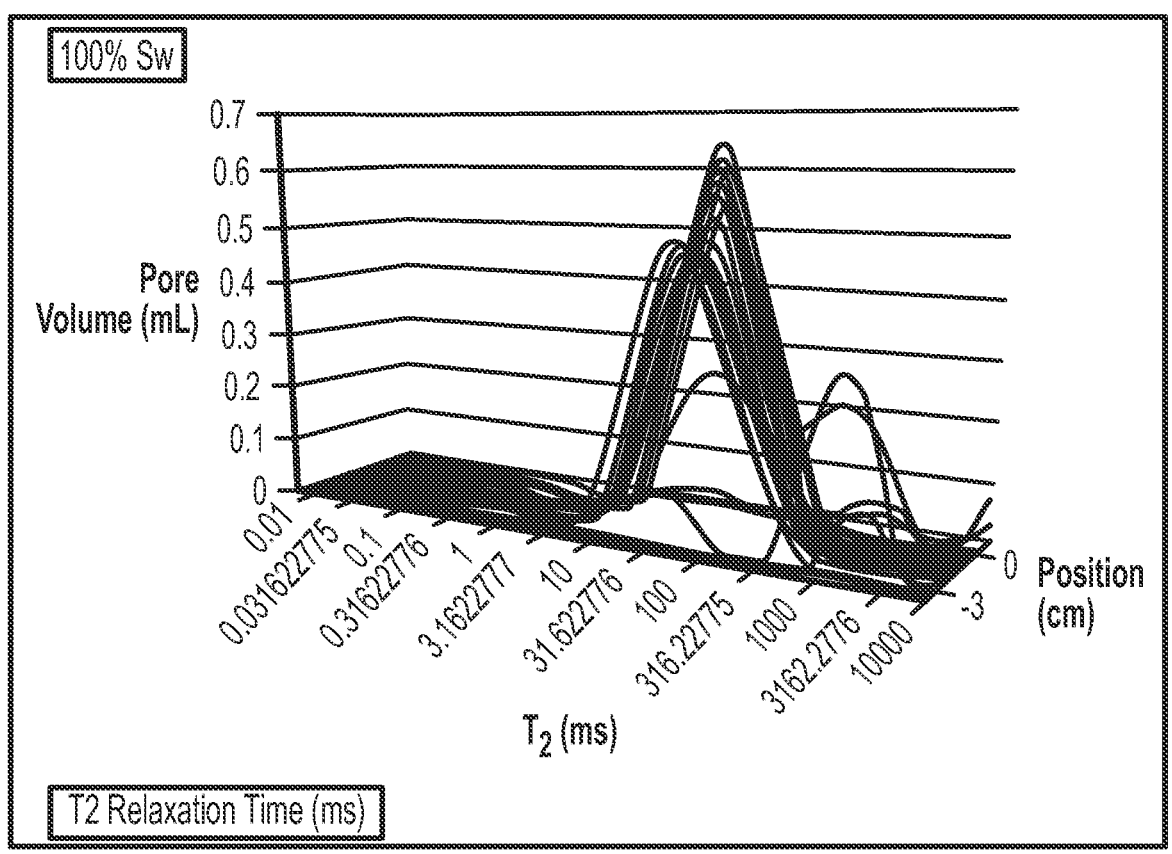

Turning to FIG. 5, FIG. 5 shows an example of spatial T2 distribution chart in accordance with one or more embodiments. In particular, the chart shown in FIG. 5 displays T2 signals with respect to a pore volume distribution for each position sampled during a T2 mapping NMR test. More specifically, a total pore volume at a sampling position may be determined from a spatial T2 distribution chart of a fully $H_2O$ saturated sample similar to the one shown in FIG. 5. For each value on the position axes, a total pore volume at a corresponding sampling position may be determined by summing all points in the pore volume distribution curve.

Figure 6:
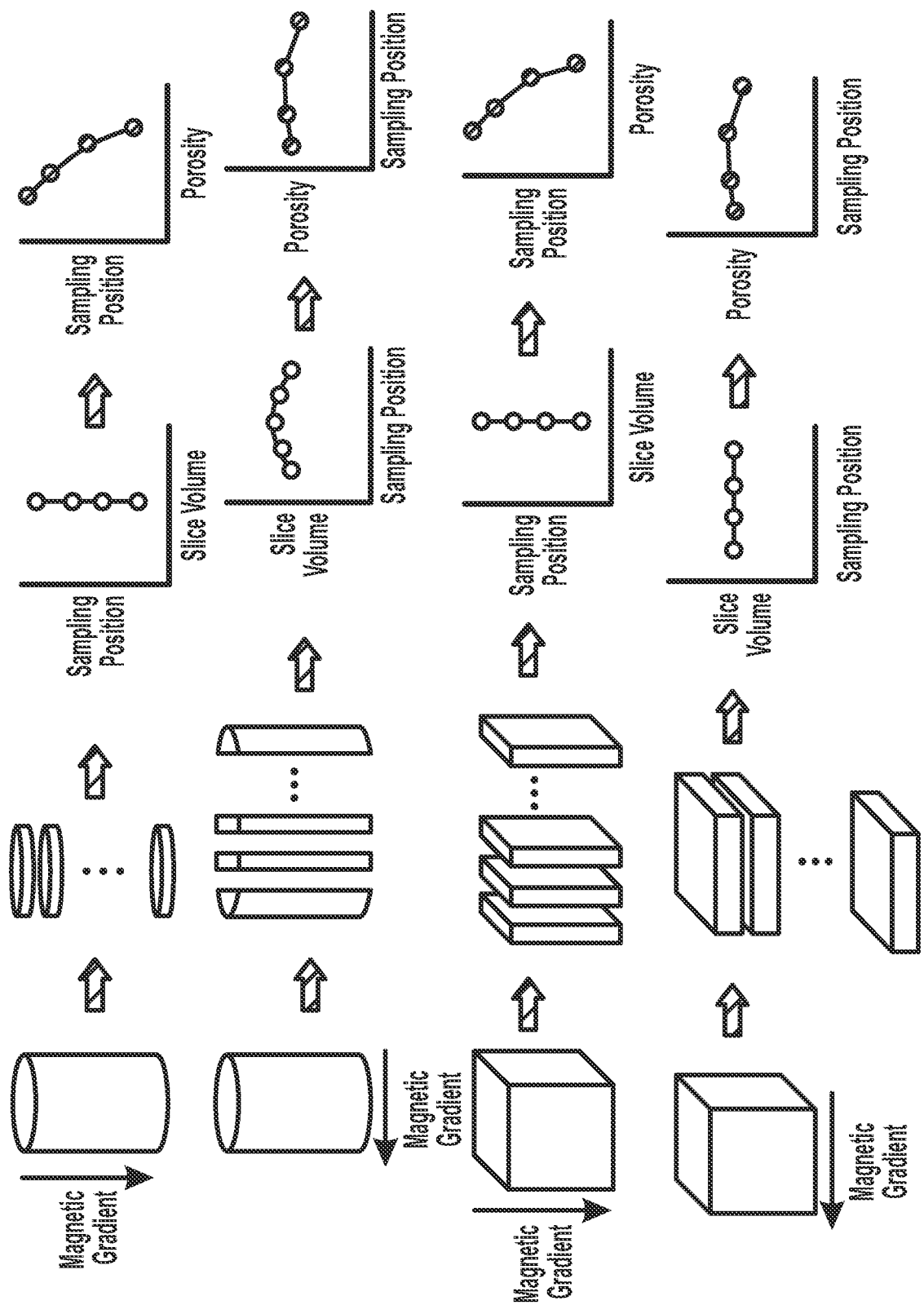

Turning to FIG. 6, FIG. 6 shows various porosity profiles determined for different directions in accordance with one or more embodiments. As shown in FIG. 6, a sampled volume of core slices for a core sample may be determined using a magnetic gradient direction and a shape of porous media. For example, the thickness of each sampled slice may be equal to the distance between each point in the position axes of FIG. 6. Thus, spatial dimensions (e.g., height and cross sectional length) of a core sample may be measured prior to an NMR laboratory test, and the dimensions may be used in addition to the sampled slice thickness to determine the sampled slice volume. While a cube shape is shown in FIG. 6, many embodiments analyze a cylindrically-shaped core sample.

Returning to FIG. 2, in Block 220, NMR data are obtained for a desaturated core sample regarding a geological region of interest in accordance with one or more embodiments. For example, NMR data may describe a distribution of T2 cutoff times at different sampling locations of a desaturated core sample. The NMR data may be acquired using an NMR spectroscopy tool during a laboratory analysis similar to the NMR spectroscopy tools described above in FIG. 1 and the accompanying description. In some embodiments, a saturated core sample is desaturated to an irreducible saturation level ($S_{wirr}$). For example, the irreducible saturation level may be where water is bound by capillary forces such that water cannot move in the desaturated core sample. A desaturation operation may be conducted with a centrifuge or a porous plate. For a centrifuge, the saturation distribution along the core sample may be derived using the following equation:

$$S_w = (1 - S_{wirr}) \left( \frac{\Delta\rho\omega^2 (r_1^2 - r^2)}{2P_e} \right)^{-\lambda} + S_{wirr} \qquad \text{Equation (2)}$$

where $S_w$ is the water saturation, $S_{wirr}$ is the irreducible water saturation, $\Delta\rho$ is the density difference of two fluids, $r_1$ is the distance from the rotation center to the outlet face of the core sample, and r is the distance from the rotation center to any point in the core sample, ω is the rotational speed of the centrifuge, and $P_e$ and λ are fitting parameters of a capillary model. To reach an irreducible saturation state, the centrifuge may achieve a spinning speed that is sufficiently high, such that the term with the negative power in Equation (2) can be neglected, which leaves us with $S_w=S_{wirr}$, indicating that irreducible water saturation has been reached. For sample, a core sample may be spun for 8 hours to reach the desirable saturation state at a predetermined rotational speed. Also, the core sample may be re-spun for another 8 hours at the same speed after switching the sample position in the centrifuge to reduce end-effects in the saturation distribution that are associated with the centrifuge technique.

While spinning porous media using a porous plate method may require more time (e.g., months before reaching irreducible water saturation state) than a desaturation operation with a centrifuge, porous plate techniques may not suffer from various centrifuge end-effects. For a tight core sample with nano-Darcy (ND) permeability, for example, a complete desaturation of the core sample may be performed using a porous plate method. However, the maximum capillary pressure and minimum saturation that can be achieved using a porous plate technique may be limited by the type of the porous plate.

In some embodiments, a spatial T2 measurement is obtained for a desaturated core sample with identical vertical resolution as the saturated core sample. For example, the spatial T2 measurement data may be used to determine the immovable/irreducible water saturation in each slice of the core sample by obtaining T2 cutoff values for each of the T2 distribution curves (e.g., as shown in FIG. 5). Likewise, T2 cutoff values may be determined for each of the T2 distribution curves such that the T2 cutoff value may correspond to the immovable/irreducible water saturation in each core sample slice. The type of cutoff may also depend on the permeability model (e.g., a T2 log-mean method or an analysis of a magnetic resonance imaging log). For illustration purposes, the cutoff value of Carbonate porous media may be around 90 mSec while T2 cutoff value may be around 30 mSec for sandstone. Similar to the spatial porosity profiles, spatial permeability profiles may be generated for each T2 distributions using spatial permeability data for different sampling positions of a core sample.

In Block 230, spatial permeability data are determined using NMR data regarding a desaturated core sample in accordance with one or more embodiments. For example, various permeability models may be used for predicting water or brine permeability from NMR data for fractured and vugy porous media. In some embodiments, spatial permeability data is obtained for porous media with permeability values higher than milli-Darcy (mD) values.

In Block 240, a geological model is determined for a geological region of interest using spatial porosity data and spatial permeability data in accordance with one or more embodiments. In some embodiments, a reservoir simulator may generate various porosity-permeability cross-plots from spatial porosity data and spatial permeability data. The spatial data may be disposed in cross-plots to fit the spatial data with an appropriate geological model using a fitting process, such as linear or nonlinear fitting techniques. Examples of fitting processes may include least square regression techniques, quadratic curve fittings, or curve fittings using logarithmic functions. In some embodiments, a geological model includes a petrophysical rock type that is identified from single core sample. Thus, spatial porosity data and spatial permeability data may be used to determine geological models for fragile and weak formations by reducing the number of measurement points for generating the geological model. Likewise, spatial porosity data and/or spatial permeability data may also be used for monitoring changes in various petrophysical rock type that may occur when a reservoir formation is treated with formation damaging chemicals (e.g., acid wash), or in enhanced oil recovery projects that inject chemicals and gases which may react with a rock matrix in a geological region.

In some embodiments, the accuracy of the fitting process is evaluated using a total number of outliners and a coefficient of determination (e.g., an $R^2$ value). In some embodiments, different petrophysical rock types have distinct geological models. Additionally, geological models and/or rock types may be determined using porosity-permeability cross-plots without data fitting. Examples of various rock types may include a linear-type fit, an exponential-type fit, a power-type fit, an uncorrelated porosity-permeability fit, a polynomial-type fit, and a logarithmic-type fit.

Figure 7:
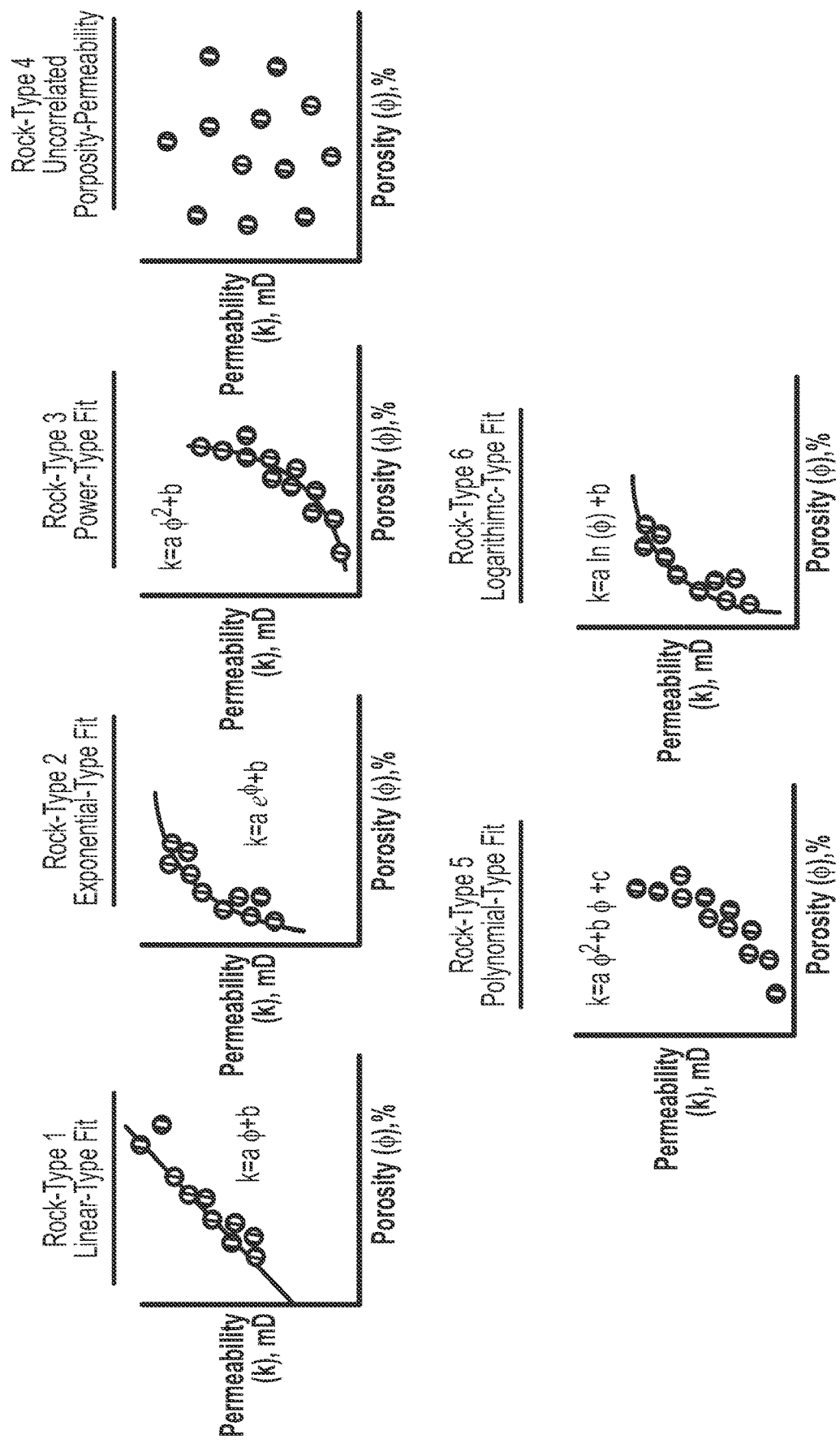

Turning to FIG. 7, FIG. 7 shows various petrophysical rock types in accordance with one or more embodiments. In FIG. 7, various porosity-permeability cross-plots are shown for different rock types based on various fitting processes using various fitting parameters (i.e., fitting parameter a, fitting parameter b, and fitting parameter c). Examples of rock types may include a linear fit, an exponential fit, a power fit, an uncorrelated porosity-permeability fit, a polynomial fit, and a logarithmic fit.

In Block 250, a hydrocarbon exploration or production operation is performed using a geological model in accordance with one or more embodiments. In particular, a geological model that identifies one or more rock types may be used in a recovery operation and for managing reservoir production. For example, carbonate, fluvial and glacial sandstones may have inhomogeneous and anisotropic pore structures (e.g., formations with thin cross-bedding) that may be described using a geological model based on spatial porosity data and spatial permeability data. Thus, a well path may be determined by one or more control systems with fewer core samples. In some embodiments, a command for a control system may be fashioned correspond to a particular drilling parameter value or production operation value. Thus, the command may be a control signal, e.g., generated by a control system, or a network message that adjusts one or more drilling parameters (e.g., a rate of penetration within a particular formation) or a production operation parameter (e.g., an optimum production flow). For example, a command may be transmitted from a reservoir simulator or control system at a well site to one or more well systems, such as drilling systems. The drilling system may be similar to the drilling system (110) described above in FIG. 1 and the accompanying description.

In some embodiments, the geological model is used to determine a particular production operation at a producing well. For example, a geological model may be used to determine reservoir properties for different geological regions. Accordingly, reservoir simulations may be performed to determine the effect of different production rates on the reservoir. Thus, one or more production operations may be optimized using the geological model.

Figure 8:
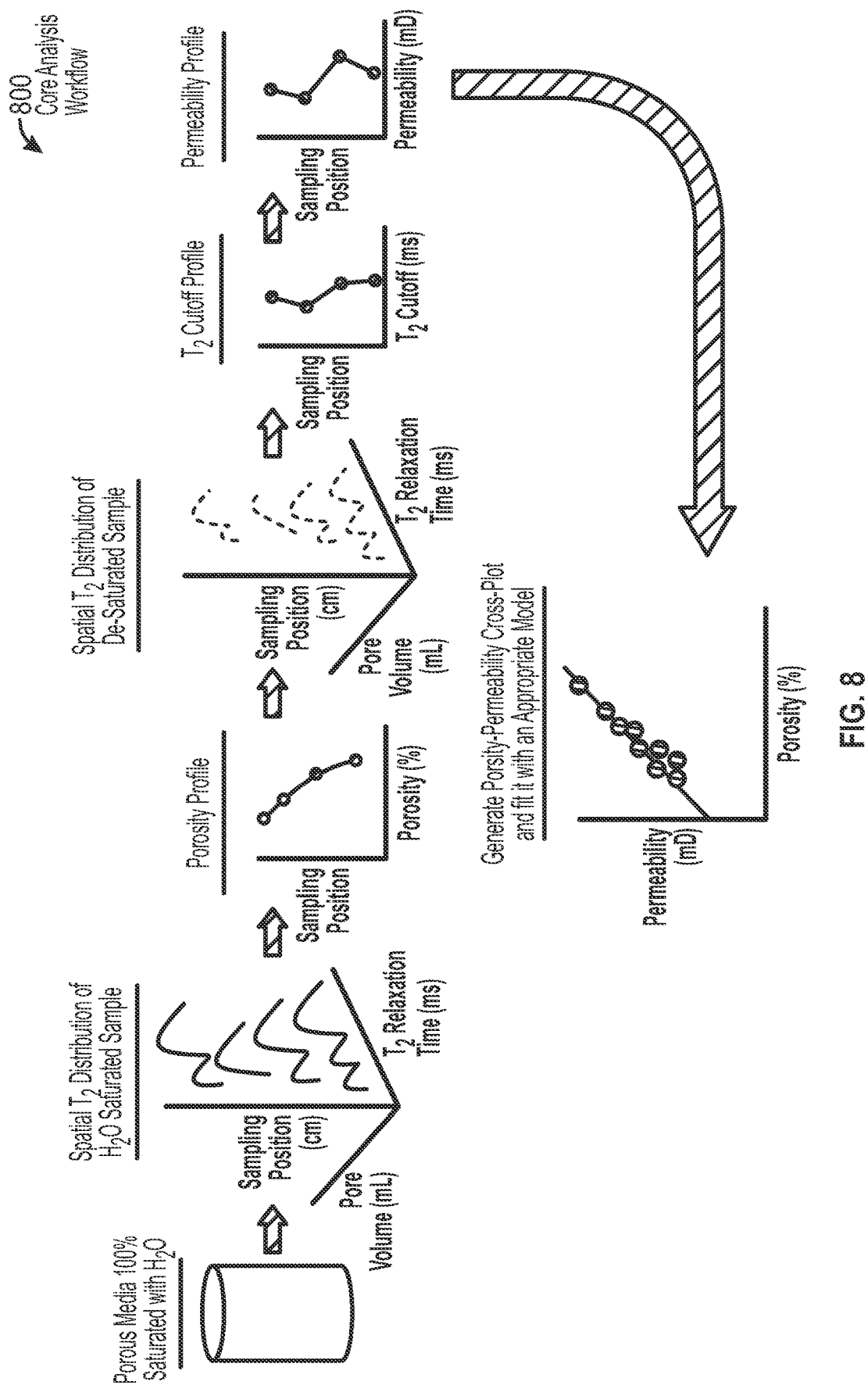
Figure 9:
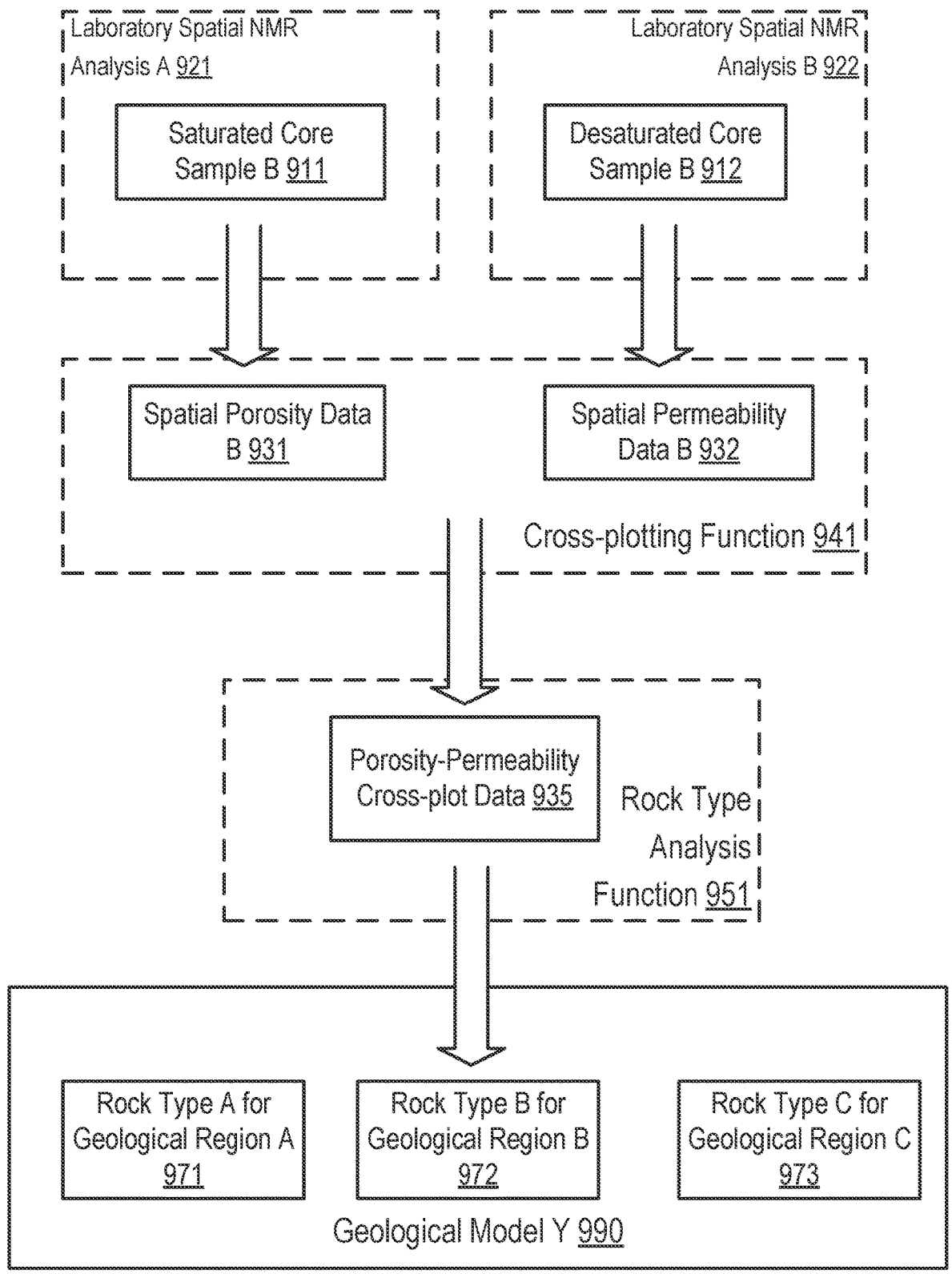

Turning to FIGS. 8 and 9, FIGS. 8 and 9 provides examples of determining a geological model using spatial porosity data and spatial permeability data in accordance with one or more embodiments. The following examples are for explanatory purposes only and not intended to limit the scope of the disclosed technology. In FIG. 8, a core analysis workflow (800) is shown that is similar to the workflow described in FIG. 2 and the accompanying description. In the core analysis workflow (800), a porous media core sample is 100% saturated with water. A reservoir simulator (not shown) obtains various spatial distributions of NMR data that are functions of relaxation time and sampling positions of pore volume of the core sample. The reservoir simulator then generates a porosity plot that is a function of sampling position. Next, the reservoir simulator obtains spatial distributions of NMR data from a desaturated core sample to produce a T2 cutoff profile as a function of sampling position. Using the T2 cutoff profile, a permeability profile is generated by the reservoir simulator where permeability in the core sample is a function of sampling position. Afterwards, a cross-plot that describes spatial porosity and spatial permeability is determined, which the reservoir simulator fits to a particular geological model.

Turning to FIG. 9, an NMR spectroscopy tool (not shown) performs a laboratory spatial NMR analysis A (921) on a saturated core sample B (911), and a laboratory spatial NMR analysis B (922) on a desaturated core sample B (912), which is the saturated core sample B (911) after a desaturation operation. As such, the NMR spectroscopy tool produces NMR data using the spatial NMR analysis A (921) and the spatial NMR analysis B (922). A reservoir simulator (not shown) uses the NMR data to produce spatial porosity data B (931) and spatial permeability data B (932). The reservoir simulator then applies a cross-plotting function (941) to the spatial porosity data B (931) and the spatial permeability data B (932) to produce a porosity-permeability cross-plot data (935). Next, the reservoir simulator applies a rock type analysis function (951) to determine a rock type B for geological region B (972). Finally, the reservoir simulator generates a geological model Y (990) that includes rock type information for different geological regions of the geological model Y (990), i.e., rock type A for geological region A (971), rock type B for geological region B (972), and rock type C for geological region C (973).

Figure 10:
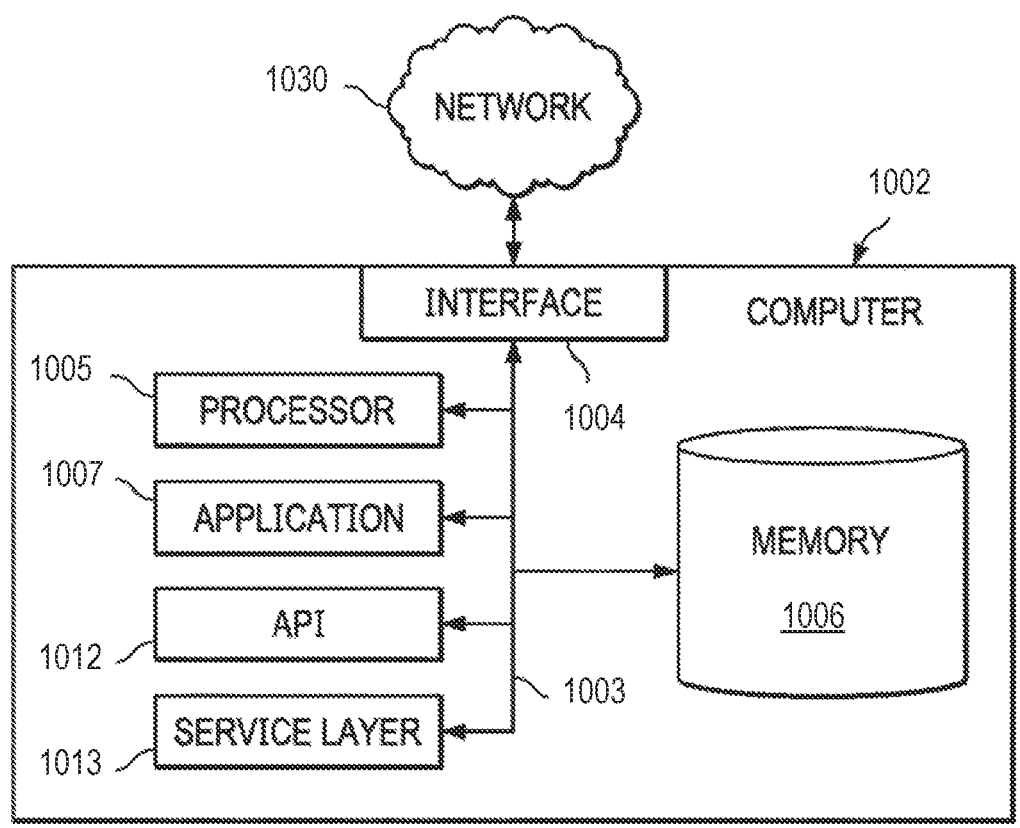
FIG. 10 shows a computer system in accordance with one or more embodiments.

Embodiments may be implemented on a computer system. FIG. 10 is a block diagram of a computer system (1002) used to provide computational functionalities associated with described algorithms, methods, functions, processes, flows, and procedures as described in the instant disclosure, according to an implementation. The illustrated computer (1002) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (1002) may include a computer that includes an input device, such as a keypad, keyboard, touch screen, or other device that can accept user information, and an output device that conveys information associated with the operation of the computer (1002), including digital data, visual, or audio information (or a combination of information), or a GUI.

The computer (1002) can serve in a role as a client, network component, a server, a database or other persistency, or any other component (or a combination of roles) of a computer system for performing the subject matter described in the instant disclosure. The illustrated computer (1002) is communicably coupled with a network (1030). In some implementations, one or more components of the computer (1002) may be configured to operate within environments, including cloud-computing-based, local, global, or other environment (or a combination of environments).

At a high level, the computer (1002) is an electronic computing device operable to receive, transmit, process, store, or manage data and information associated with the described subject matter. According to some implementations, the computer (1002) may also include or be communicably coupled with an application server, e-mail server, web server, caching server, streaming data server, business intelligence (BI) server, or other server (or a combination of servers).

The computer (1002) can receive requests over network (1030) from a client application (for example, executing on another computer (1002)) and responding to the received requests by processing the said requests in an appropriate software application. In addition, requests may also be sent to the computer (1002) from internal users (for example, from a command console or by other appropriate access method), external or third-parties, other automated applications, as well as any other appropriate entities, individuals, systems, or computers.

Each of the components of the computer (1002) can communicate using a system bus (1003). In some implementations, any or all of the components of the computer (1002), both hardware or software (or a combination of hardware and software), may interface with each other or the interface (1004) (or a combination of both) over the system bus (1003) using an application programming interface (API) (1012) or a service layer (1013) (or a combination of the API (1012) and service layer (1013). The API (1012) may include specifications for routines, data structures, and object classes. The API (1012) may be either computer-language independent or dependent and refer to a complete interface, a single function, or even a set of APIs. The service layer (1013) provides software services to the computer (1002) or other components (whether or not illustrated) that are communicably coupled to the computer (1002). The functionality of the computer (1002) may be accessible for all service consumers using this service layer. Software services, such as those provided by the service layer (1013), provide reusable, defined business functionalities through a defined interface. For example, the interface may be software written in JAVA, C++, or other suitable language providing data in extensible markup language (XML) format or other suitable format. While illustrated as an integrated component of the computer (1002), alternative implementations may illustrate the API (1012) or the service layer (1013) as stand-alone components in relation to other components of the computer (1002) or other components (whether or not illustrated) that are communicably coupled to the computer (1002). Moreover, any or all parts of the API (1012) or the service layer (1013) may be implemented as child or sub-modules of another software module, enterprise application, or hardware module without departing from the scope of this disclosure.

The computer (1002) includes an interface (1004). Although illustrated as a single interface (1004) in FIG. 10, two or more interfaces (1004) may be used according to particular needs, desires, or particular implementations of the computer (1002). The interface (1004) is used by the computer (1002) for communicating with other systems in a distributed environment that are connected to the network (1030). Generally, the interface (1004) includes logic encoded in software or hardware (or a combination of software and hardware) and operable to communicate with the network (1030). More specifically, the interface (1004) may include software supporting one or more communication protocols associated with communications such that the network (1030) or interface's hardware is operable to communicate physical signals within and outside of the illustrated computer (1002).

The computer (1002) includes at least one computer processor (1005). Although illustrated as a single computer processor (1005) in FIG. 10, two or more processors may be used according to particular needs, desires, or particular implementations of the computer (1002). Generally, the computer processor (1005) executes instructions and manipulates data to perform the operations of the computer (1002) and any algorithms, methods, functions, processes, flows, and procedures as described in the instant disclosure.

The computer (1002) also includes a memory (1006) that holds data for the computer (1002) or other components (or a combination of both) that can be connected to the network (1030). For example, memory (1006) can be a database storing data consistent with this disclosure. Although illustrated as a single memory (1006) in FIG. 10, two or more memories may be used according to particular needs, desires, or particular implementations of the computer (1002) and the described functionality. While memory (1006) is illustrated as an integral component of the computer (1002), in alternative implementations, memory (1006) can be external to the computer (1002).

The application (1007) is an algorithmic software engine providing functionality according to particular needs, desires, or particular implementations of the computer (1002), particularly with respect to functionality described in this disclosure. For example, application (1007) can serve as one or more components, modules, applications, etc. Further, although illustrated as a single application (1007), the application (1007) may be implemented as multiple applications (1007) on the computer (1002). In addition, although illustrated as integral to the computer (1002), in alternative implementations, the application (1007) can be external to the computer (1002).

There may be any number of computers (1002) associated with, or external to, a computer system containing computer (1002), each computer (1002) communicating over network (1030). Further, the term "client," "user," and other appropriate terminology may be used interchangeably as appropriate without departing from the scope of this disclosure. Moreover, this disclosure contemplates that many users may use one computer (1002), or that one user may use multiple computers (1002).

In some embodiments, the computer (1002) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed:

1. A method, comprising:
obtaining, by a computer processor, first nuclear magnetic resonance (NMR) data for a saturated core sample regarding a geological region of interest;
determining, by the computer processor and using the first NMR data, spatial porosity data based on the saturated core sample, wherein the spatial porosity data describes a plurality of porosity values as a function of a sampling position of the saturated core sample;
obtaining, by the computer processor, second NMR data for a desaturated core sample regarding the geological region of interest;
determining, by the computer processor and using the second NMR data, spatial permeability data based on the desaturated core sample, wherein the spatial permeability data describes a plurality of permeability values as a function of the sampling position of the desaturated core sample; and
determining, by the computer processor, a geological model for the geological region of interest using the spatial porosity data, the spatial permeability data, and a fitting process.

2. The method of claim 1,
wherein the sampling position of the saturated core sample comprises a predetermined sampling direction and a plurality of sampling locations for the saturated core sample, and
wherein the plurality of sampling locations correspond to a plurality of core slices of the saturated core sample arranged according to the predetermined sampling direction, and
wherein the first NMR data and the second NMR data correspond to a plurality of magnetic gradients that are determined for the plurality of core slices.

3. The method of claim 1,
wherein the desaturated core sample is the saturated core sample after a desaturation operation, and
wherein the desaturation operation is performed using a porous plate.

4. The method of claim 1,
wherein the first NMR data comprises a distribution of T2 relaxation times at a first plurality of sampling locations of the saturated core sample, and
wherein the second NMR data comprises a distribution of T2 cutoff times at a second plurality of sampling locations of the desaturated core sample.

5. The method of claim 1,
wherein the first NMR data and the second NMR data are acquired using a plurality of laboratory analyses using an NMR spectroscopy tool.

6. The method of claim 1, further comprising:
determining, by the computer processor, a porosity-permeability cross-plot using the spatial porosity data and the spatial permeability data; and
determining, by the computer processor, a predetermined rock type for a portion of the geological region of interest using the fitting process.

7. The method of claim 6, wherein the predetermined rock type is selected from a group consisting of:
a linear fit;
an exponential fit;
a power fit;
an uncorrelated porosity-permeability fit;
a polynomial fit; and
a logarithmic fit.

8. The method of claim 1,
wherein the fitting process is a least squares regression technique.

9. The method of claim 1, further comprising:
determining, by the computer processor, a drilling operation for a drilling system based on the geological model, and
wherein the drilling operation comprises a well path based on a plurality of respective rock types for a plurality of geological regions, and
wherein the well path is determined using the geological model.

10. The method of claim 1, further comprising:
determining, by the computer processor, a production operation for a well system based on the geological model,
wherein the production operation comprises a production rate for the well system based on one or more reservoir properties of the geological region of interest.

11. A system, comprising:
a nuclear magnetic resonance (NMR) spectroscopy tool; and
a reservoir simulator comprising a computer processor, wherein the reservoir simulator is coupled to the NMR spectroscopy tool, the reservoir simulator is configured to perform a method comprising:
obtaining, using the NMR spectroscopy tool, first nuclear magnetic resonance (NMR) data for a saturated core sample regarding a geological region of interest;
determining, using the first NMR data, spatial porosity data based on the saturated core sample, wherein the spatial porosity data describes a plurality of porosity values as a function of a sampling position of the saturated core sample;
obtaining, using the NMR spectroscopy tool, second NMR data for a desaturated core sample regarding the geological region of interest;
determining, using the second NMR data, spatial permeability data based on the desaturated core sample, wherein the spatial permeability data describes a plurality of permeability values as a function of the sampling position of the desaturated core sample; and
determining a geological model for the geological region of interest using the spatial porosity data, the spatial permeability data, and a fitting process.

12. The system of claim 11,
wherein the sampling position of the saturated core sample comprises a predetermined sampling direction and a plurality of sampling locations for the saturated core sample, and
wherein the plurality of sampling locations correspond to a plurality of core slices of the saturated core sample arranged according to the predetermined sampling direction, and
wherein the first NMR data and the second NMR data correspond to a plurality of magnetic gradients that are determined for the plurality of core slices.

13. The system of claim 11,
wherein the desaturated core sample is the saturated core sample after a desaturation operation, and
wherein the desaturation operation is performed using a porous plate.

14. The system of claim 11,
wherein the first NMR data comprises a distribution of T2 relaxation times at a first plurality of sampling locations of the saturated core sample, and
wherein the second NMR data comprises a distribution of T2 cutoff times at a second plurality of sampling locations of the desaturated core sample.

15. The system of claim 11, wherein the method reservoir simulator further comprises:
determining a porosity-permeability cross-plot using the spatial porosity data and the spatial permeability data; and
determining a predetermined rock type for a portion of the geological region of interest using the fitting process.

16. The system of claim 11, further comprising:
a drilling system configured to determine a drilling operation based on the geological model, and
wherein the drilling operation comprises a well path based on a plurality of respective rock types for a plurality of geological regions, and
wherein the well path is determined using the geological model.

17. The system of claim 11, further comprising:
a well system configured to determine a production operation based on the geological model,
wherein the production operation comprises a production rate for the well system based on one or more reservoir properties of the geological region of interest.

18. A non-transitory computer readable medium storing instructions executable by a computer processor, the instructions being configured to perform, when executed by the computer processor, a method comprising:
obtaining first nuclear magnetic resonance (NMR) data for a saturated core sample regarding a geological region of interest;
determining, using the first NMR data, spatial porosity data based on the saturated core sample, wherein the spatial porosity data describes a plurality of porosity values as a function of a sampling position of the saturated core sample;
obtaining second NMR data for a desaturated core sample regarding the geological region of interest;
determining, using the second NMR data, spatial permeability data based on the desaturated core sample, wherein the spatial permeability data describes a plurality of permeability values as a function of the sampling position of the desaturated core sample; and
determining a geological model for the geological region of interest using the spatial porosity data, the spatial permeability data, and a fitting process.

19. The non-transitory computer readable medium of claim 18, wherein the sampling position of the saturated core sample comprises a predetermined sampling direction and a plurality of sampling locations for the saturated core sample, wherein the plurality of sampling locations correspond to a plurality of core slices of the saturated core sample arranged according to the predetermined sampling direction, and wherein the first NMR data and the second NMR data correspond to a plurality of magnetic gradients that are determined for the plurality of core slices.

20. The non-transitory computer readable medium of claim 18, wherein the method further comprises:

determining a porosity-permeability cross-plot using the spatial porosity data and the spatial permeability data; and determining a predetermined rock type for a portion of the geological region of interest using the fitting process.

* * * * *